United States Patent [19]

Quan et al.

[11] Patent Number: 5,258,524

[45] Date of Patent: Nov. 2, 1993

[54] BIS-BIBENZIMIDAZOLE COMPOSITION

[75] Inventors: Peter M. Quan, Rochdale; Derek Thorp, Hopwood; Raymond F. Dalton, Cheadle Hulme, all of England

[73] Assignee: Imperial Chemical Industries PLC, London, England

[21] Appl. No.: 843,405

[22] Filed: Feb. 28, 1992

[30] Foreign Application Priority Data

Mar. 1, 1991 [GB] United Kingdom ............... 9104395

[51] Int. Cl.[5] ........................................... C07D 233/54
[52] U.S. Cl. ........................ 548/335.1; 75/711; 423/DIG. 14; 548/324.1
[58] Field of Search ............... 423/DIG. 14; 75/711; 548/335, 324

[56] References Cited

U.S. PATENT DOCUMENTS 4,309,551  1/1982  Schomberger et al. ............ 548/324
4,696,801  9/1987  Devonald .................... 423/DIG. 14

FOREIGN PATENT DOCUMENTS 0027897  5/1981  European Pat. Off. .
0196153  10/1986  European Pat. Off. .

Primary Examiner—Peter D. Rosenberg
Attorney, Agent, or Firm—Cushman, Darby & Cushman

[57] ABSTRACT

A composition of bibenzimidazoles of the Formula (I):

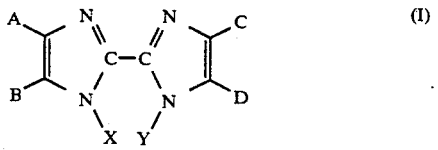

wherein
X & Y which may be the same or different and, taken together, contain a total of from 12 to 52 saturated carbon atoms, are (a) each selected from —R, —COR, —CH$_2$COOR, —CH(COOR)$_2$ and —COOR; or (b) together form a group selected from

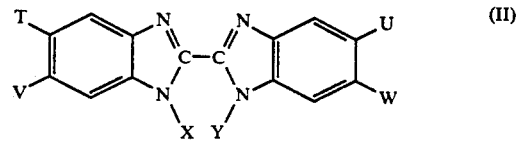

wherein
R is an optionally substituted hydrocarbyl group,
A & B taken together with the two carbon atoms to which they are linked form an optionally substituted benzene ring; and
C & D taken together with the two carbon atoms to which they are linked form an optionally substituted benzene ring;
characterised in that at least 50% by weight of the bibenzimidazoles in the composition are of Formula (II)

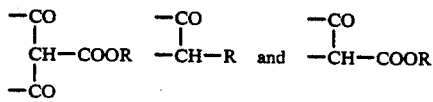

wherein
X and Y are as hereinbefore defined;
T, U, V & W which may be the same or different, are H, R$^1$ or OR$^1$ provided at least one of T, U, V & W is R$^1$ or OR$^1$;
and R$^1$ is C$_{1-6}$-alkyl;
which are suitable for use in the extraction of zinc from aqueous solutions of zinc in the presence of other metals.

14 Claims, No Drawings

BIS-BIBENZIMIDAZOLE COMPOSITION

The present invention relates to a composition of bis-bibenzimidazoles and their use in the extraction of metals from aqueous solutions of metal salts.

The use of solvent extraction techniques for the hydrometallurgical recovery of metals from metal ores has been practised commerically for a number of years. Thus, copper can be recovered from oxide ores or from ore tailings by treating the crushed ore with dilute sulphuric acid to give an aqueous solution of copper sulphate which is subsequently contacted with a solution in a water-immiscible organic solvent of a metal extractant whereby the copper values are selectively extracted into the organic phase.

The application of solvent extraction techniques to aqueous solutions containing halide anions however has presented numerous technical problems. More specifically copper bearing sulphur-containing ores such as chalcopyrite may be leached using ferric chloride or cupric chloride solutions, but the selective solvent extraction of the resultant leach solutions presents formidable difficulties. The recovery of zinc by solvent extraction from halide-containing solutions such as those derived from sulphur-containing ores by chloride leaching has also been proposed (see for example, G. M. Ritcey, B. H. Lucas and K. T. Price, Hydrometallurgy, 1982, 8, page 197). However, known extractants for zinc (for example organophosphorous compounds such as tributyl phosphate) generally show a poor efficiency of metal recovery and a poor selectivity for zinc over the iron present in such leach solutions.

EP 196153A discloses certain bi-imidazole derivatives, including bi-benzimidazole derivatives, and their use as extractants of metals from halide-containing solutions. These extractants are effective for the extraction of zinc from halide solutions. However, the bi-imidazole derivatives extract a substantial proportion of both copper and zinc and hence do not show a useful selectivity for zinc relative to copper. The bi-benzimidazole derivatives are more selective but the proportion of zinc extracted from the aqueous phase is relatively low, particularly with the composition of Example 6 which is a mixture of compounds containing two methyl groups in various positions on the peripheral benzene rings.

It has now been found that bibenzimidazoles having certain substituents at the 5, 5′, 6 and/or 6′ positions, and compositions containing a high proportion of such compounds are significantly better metal extractants than the corresponding compounds in which the 5, 5′, 6 and 6′ positions are unsubstituted.

According to a first aspect of the present invention there is provided a composition of bibenzimidazoles of the Formula (I):

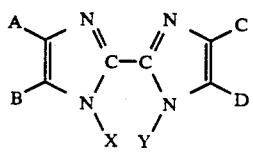

wherein

X & Y which may be the same or different and, taken together, contain a total of from 12 to 52 saturated carbon atoms, are (a) each selected from —R, —COR, —CH$_2$COOR, —CH(COOR)$_2$ and —COOR; or (b) together form a group selected from

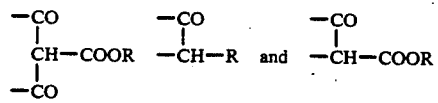

wherein R is an optionally substituted hydrocarbyl group;

A & B taken together with the two carbon atoms to which they are linked form an optionally substituted benzene ring; and C & D taken together with the two carbon atoms to which they are linked form an optionally substituted benzene ring; characterised in that at least 50% by weight of the bibenzimidazoles in the composition are of Formula (II):

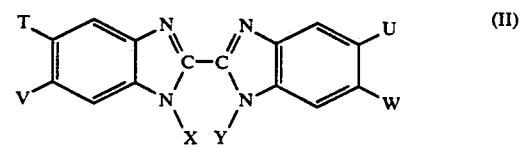

wherein

X and Y are as hereinbefore defined;

T, U, V & W which may be the same or different, are H, R$^1$ or OR$^1$ provided at least one of T, U, V & W is R$^1$ or OR$^1$; and and R$^1$ is C$_{1-6}$-alkyl.

The optional substituents on the benzene ring formed by A and B or C and D include C$_{1-6}$-alkyl, especially methyl and C$_{1-6}$-alkoxy, especially methoxy.

It is preferred that at least 75%, and more especially at least 90%, of the bibenzimidazoles in the composition are of Formula II.

According to a second aspect of the present invention there is provided a composition comprising a compound of formula (IIa) and a compound of formula (IIb) in a weight ratio of at least 3 to 1, respectively.

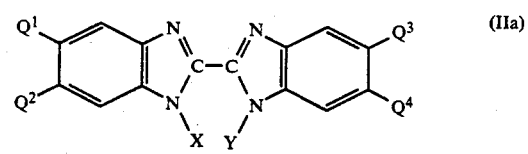

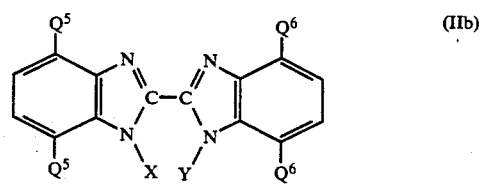

wherein

Q$^1$, Q$^2$, Q$^3$ and Q$^4$ are each independently H, alkyl or alkoxy;

X and Y are as hereinbefore defined; and one of the groups represented by Q$^5$ and one of the groups represented by Q$^6$ are each methyl and all remaining groups represented by Q$^5$ and Q$^6$ are H; provided that at least one of Q$^1$, Q$^2$, Q$^3$ and Q$^4$ is alkyl or alkoxy.

It is preferred that said weight ratio of the compound of Formula (IIa) to the compound of Formula (IIb) is at least 5:1, more preferably at least 10:1, especially at least 50:1.

In the compound of Formula (IIa), it is preferred that at least two of $Q^1$, $Q^2$, $Q^3$ and $Q^4$ are alkyl or alkoxy because such a compound is a particularly powerful metal extractant. In another preferred compound of Formula (IIa) $Q^1$, $Q^2$, $Q^3$ and $Q^4$ are each independently alkyl or alkoxy.

The preferred alkyl or alkoxy groups represented by $Q^1$, $Q^2$, $Q^3$ or $Q^4$ are respectively $C_{1-6}$-alkyl or $C_{1-6}$-alkoxy, especially methyl or methoxy.

Compositions comprising compounds of formula (IIa) which are free, or substantially free, from any compound of formula (IIb) are included in the second aspect of the present invention.

In the compounds of the present composition, the group R is preferably alkyl, alkylaryl, aralkyl, or cycloalkyl, each of which may be substituted by a group which does not adversely affect the solubility of the compounds in the non-polar organic solvents used in solvent extraction processes. Examples of suitable substituent groups include alkyl, alkoxy and cycloalkyl, especially those containing up to 8 carbon atoms, and halogen. It is further preferred that each R is branched alkyl, especially branched $C_{8-24}$-alkyl, provided that X & Y, taken together, contain from 12 to 52 saturated carbon atoms. As X and Y in Formulae (I) & (II) or (IIa) and (IIb) may be the same or different, they may contain different R groups.

It is preferred that X & Y are the same and that each is —COOR. It is especially preferred that X & Y are both —COOR wherein R is a branched chain alkyl group containing from 8 to 24 carbon atoms. Improved solubility in the relevant non-polar organic solvents is often displayed where groups represented by R in the same molecule or in different molecules within the compositions are isomeric alkyl groups with different patterns of branching.

It is further preferred that each R is a branched primary alkyl group. The term "branched primary alkyl group" is used herein to mean a branched alkyl group bearing two hydrogen atoms on the carbon atom linked to the oxygen atom in the group —COOR. Compounds of Formula (II) and (IIa) and compositions containing a high proportion of such compounds, in which each group R is a branched primary alkyl group have been found to exhibit a high affinity for zinc and enhanced selectivity against acid transfer and the transfer of undesired metals.

Branched primary alkyl groups R are conveniently derived from commercially available mixtures of branched aliphatic alcohols manufactured by the 'Oxo' process or from branched alcohols prepared by the Guerbet and Aldol condensations. Such Guerbet alcohols are primary alcohols characterised by branching at the position beta to the hydroxyl group and have the Formula (III):

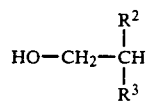

(III)

wherein $R^2$ and $R^3$ are both alkyl groups and one of the groups $R^2$ and $R^3$ contains two fewer carbon atoms than the other one of groups $R^2$ and $R^3$.

The Guerbet alcohols generally comprise a mixture of compounds of Formula (III) which differ in the chain length or branching pattern of $R^2$ and/or $R^3$, each of which may be straight or branched chain alkyl groups. A mixture of highly branched primary alcohols may be obtained by Guerbet or Aldol condensations of mixtures of alcohols and aldehydes respectively. Good solubility in organic solvents, especially the hydrocarbon solvents which are generally used in a commercial solvent extraction process, is conferred on the bibenzimidazole compounds of the present compositions when each group R is derived from decanol, tridecanol or a commercial isooctadecanol. If the group R is derived from a commercial isooctadecanol, this is conveniently isooctadecanol obtained by the aldol dimerisation of commercial nonanol and believed to consist essentially of a mixture of geometrical isomers of the compound of Formula (IV):

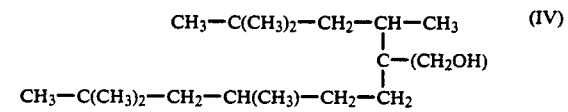

Guerbet alcohols may be used directly to form the group —COOR by reaction to form a chloroformate derivative which is then reacted with a 2,2'-bibenzimidazole having no substituents in the 1,1'-positions. Alternatively, the alcohols may be oxidised to carboxylic acids and thence converted to the corresponding acid chloride to introduce a group —CO.R, for example by reaction with a 2,2'-bibenzimidazole as described hereafter. However, when the Guerbet alcohol is oxidised to the corresponding carboxylic acid, the derived alkyl group R will be a branched secondary alkyl group rather than a branched primary alkyl group as present in the Guerbet alcohol of Formula (III).

When two of T, U, V & W are $R^1$ or $OR^1$, these may be in the same benzene ring but are preferably in different benzene rings. It is preferred that each benzene ring in the bibenzimidazole of Formula (II) or (IIa) carries one or two substituents, i.e. that at least one of T & V and at least one of U & W is a group $R^1$ or $OR^1$ and more especially $R^1$. It is preferred that $R^1$ is $C_{1-4}$-alkyl, especially methyl. Although preferred compounds of Formula (II) or (IIa) have at least one substituent on each benzene ring, the compounds of Formula (II) or (IIa) may have one, two, three or four substituents of this type. Typically the present composition comprises a mixture of isomeric or homologous compounds which differ in respect of the location of the substituent, or substituents, $R^1$ and $OR^1$ on the benzene rings.

Examples of preferred dimethyl compounds of Formula (II) or (IIa) are:

1,1'-bis(tridecyloxycarbonyl)-5(6),5'(6')-dimethyl-2,2'-bibenzimidazole;

1,1'-bis(isodecyloxycarbonyl)-5(6),5'(6')-dimethyl-2,2'-bibenzimidazole; and 1,1'-bis(isooctadecyloxycarbonyl)-5(6),5'(6')-dimethyl-2,2'-bibenzimidazole.

A compound of Formula (II) or (IIa) in which at least one of T, U, V and W is OR is new and forms a sub-feature of the present invention.

A compound of Formula (II) or (IIa) in which each of T, U, V & W is a substituent, $R^1$ or $OR^1$ is new and form a sub-feature of the present invention. Examples of preferred tetra-methyl compound types are:

1,1'-bis(tridecyloxycarbonyl)-5,6,5',6'-tetramethyl-2,2'-bibenzimidazole;

1,1'-bis(isodecyloxycarbonyl)-5,6,5',6'-tetramethyl-2,2'-bibenzimidazole; and 1,1'-bis(isooctadecyloxycarbonyl)-5,6,5',6'-tetramethyl-2,2'-bibenzimidazole.

2,2'-Bibenzimidazole compounds and compositions for use in the preparation of the present compounds and compositions may be prepared by reaction of an o-phenylenediamine carrying appropriate substituents in the 4- or 4- and 5-positions, with an appropriate oxalic acid derivative. Suitable oxalic acid derivatives include trichloroacetonitrile or methyl trichloroacetamidate (see Holan, Ennis and Hinde, J. Chem Soc (London), (C) 1967 page 20).

The compounds and compositions of Formulae (I), (II), (IIa) or (IIb) may be prepared by reaction of such 2,2'-bibenzimidazole with appropriate alkyl or acyl halides or alkylchloroformates to introduce the X and Y.

The present compounds and compositions (hereinafter referred to as "extractants") are suitable for extracting metals from aqueous solutions containing metal salts by contacting the aqueous solution with a solution of the compound or composition in a water-immiscible organic solvent.

The present extractants are especially useful for the extraction of metals from aqueous solutions of metal salts containing halide or pseudo halide anions. The term "pseudo halide" is used herein to mean anions derived from compounds which show a resemblance to the halogens in their reactions and in the properties of their anions. Examples of such compounds are cyanogen, oxy-, thio- and seleno-cyanogen and the azide radical.

The metal salts present in the aqueous solution may be salts of zinc, iron, copper, lead or cadmium. The present extractants are especially suitable for the extraction of zinc from liquors containing zinc salts.

Thus, the extraction process using an extractant according to the present invention may be used to extract any metal, especially zinc, capable of forming a stable halide- or pseudohalide-complex with the bibenzimidazole compound in a water-immiscible organic solvent, from an aqueous solution containing the desired metal and a second metal which does not complex or only weakly complexes with the extractant in the form of its halide or pseudohalide. Examples of second metals include iron, lead, and cadmium. The extraction process is especially suitable for the solvent extraction of zinc from an aqueous solution obtained by the halide or pseudohalide leaching of sulphur containing ores of zinc, especially the complex sulphide ores. In general, such ores, especially in the case of 'complex' ores contain zinc in combination with other metals, especially lead and/or copper in relative proportions which vary from ore to ore. In the case of a solution obtained by leaching a complex ore containing both copper and zinc, it is convenient to recover both the copper and the zinc in successive processing stages from the leach solutions. More specifically, copper may be recovered from the leach solution by solvent extraction and the raffinate from this process may be treated in a separate solvent extraction process for the recovery of zinc. Typically, the present extractant is used in the zinc extraction stage and another solvent extractant, such as a compound disclosed in EP 57,797A, is used in the copper extraction stage.

Leaching of the ore can be effected using any suitable technique including, but not limited to, ferric chloride leaching, direct chlorination or oxidation in the presence of sodium chloride.

The present extraction process may be incorporated into a wide variety of different methods for the overall recovery of metals from their ores or from other metal-bearing sources. Details of these methods will vary depending on the metal concerned and the nature and composition of the leach solution. By way of example, an integrated process which is especially suitable for leach solutions containing high levels of cupric ion is described in EP 57,797A.

The present extractants are especially useful for the recovery of zinc by solvent extraction. Thus the present extactants in general have a high affinity for zinc and in general this is combined with an excellent selectivity for zinc over acid and iron which are inevitably present in the leach solution, especially when ferric chloride is used as leachant. However, compounds which have a high affinity for zinc may also have a significant affinity for copper, and such compounds are not truly selective for zinc in the presence of high levels of copper. This is not a significant disadvantage in commercial operation, even when it is desired to recover zinc from a solution containing both copper and zinc, since the recovery of zinc generally takes place after the bulk of copper has been removed, for example in a first solvent extraction stage. If the presence of more than a small amount of copper in the aquous solution containing the zinc (such as 1%, 0.01% or even 0.005% w/v) is likely to have a deleterious effect on the extraction and recovery of zinc, it is desirable to remove any residual copper remaining in the aqueous solution to a level at which the deleterious effect does not occur (by, for example, cementation of the copper using a metal such as zinc or iron) and to treat the essentially copper-free aqueous solution by solvent extraction to recover the zinc.

The zinc solvent extraction circuit may be similar in design to that proposed in EP 57797A for the recovery of copper from halide-containing solutions by solvent extraction. Thus, in a circuit for the recovery of both copper and zinc from the aqueous leach solution derived from the leaching of a sulphur-containing ore with for example ferric chloride, the aqueous low-copper raffinate from the copper solvent extraction stage will contain zinc, iron and halide ion (for example, Zn: 35 to 60 gdm$^{-3}$; Fe: 70 to 120 gdm$^{-3}$ and Cl$^+$: 3.5M to 6.0M; and HCl: 5 gdm$^{-3}$) and preferably <0.01% w/v copper. This feed to the zinc circuit may be contacted with a solution of the present extractant in a water immiscible organic solvent into which the zinc is extracted. The loaded organic phase solution is contacted with an aqueous strip solution, which may optionally contain zinc and halide ion, such that at least a proportion of the zinc transfers into the aqueous strip phase. The stripped organic phase is returned to extract more zinc, and the loaded aqueous strip solution is passed to a zinc recovery stage, typically an electrowinning stage. The electrowinning stage may produce metallic zinc and chlorine gas (see 'Zinc Electrowinning from Chloride Electrolyte' by D. J. MacKinnon and J. M. Brannen; Mining Engineering April 1982, p 409) which may be used to regenerate the ferric chloride leachant, now reduced to ferrous chloride. Alternatively an internal regeneration of the leachant may take place in a split cell without the generation of free chlorine gas. The aqueous stream from the electrowinning stage, depleted of zinc and chloride ion, is returned to the strip stage to act as the aqueous strip solution, thereby completing the zinc extraction circuit.

The extraction step is conveniently effected at ambient temperature, for example 15° C. to 25° C. However, the effectiveness of stripping is enhanced at elevated temperatures, for example 40° C. to 80° C., and it is advantageous to effect the stripping operation at a higher temperature, conveniently 60° C. to 65° C.

An extraction process using the present extractant may be represented by an equation such as the following:

$$L_{org} + M^{++}_{aq} + 2Cl^-_{aq} \rightleftharpoons (LMCl_2)_{org}$$

wherein
M is a divalent metal ion such as zinc;
L is the extractant; and $(LMCl_2)$ is the solvent soluble complex of metal and extractant Although this equation is an oversimplified representation of a very complex process and should not be taken as in any way limiting the scope of the present invention, it serves to illustrate the formation of a neutral organic phase complex of the divalent metal and the extractant (L). Under certain extraction conditions there is evidence that the extracted complex has the formula $(LMCl_2)_2$. This process is believed to predominate in the extraction process using the present extractant. The equation illustrates the reversible nature of the extraction process, whereby the complex of the metal and the extractant in the organic phase can be stripped on contact with an aqueous solution from which the metal and halide ion can be removed in a subsequent electrowinning stage.

A further property which is of importance for the present extraction process is the absence of significant protonation of the extractant by the acidic leach liquor. Such protonation may be represented by the equation:

$$L_{org} + H^+_{aq} + Cl^-_{aq} \rightleftharpoons (LH^+Cl^-)_{org}$$

wherein
L is the extractant; and $(LH^+Cl^-)$ is the solvent soluble protonated extractant.

Such protonation of an extractant carries hydrochloric acid, or metals which can form a complex chloro anion, into the organic phase and thereby reduces selectivity at the extraction and strip stages. This problem is particularly acute with zinc which is believed to promote such acid transfer. However, the present extractant does not exhibit this effect to any significant extent, combining a high affinity for zinc with a low degree of protonation.

EP 196153A discloses the use of bi-imidazola derivatives for the extraction of zinc from aqueous solution. The bi-imidazole extractant described in Example 1 of EP 196,153A was shown to extract at least 97% of the zinc from the aqueous feed solution, but has been shown to form a strong complex with zinc from which the zinc is not readily stripped when the organic phase is contacted with an aqueous strip solution. On the other hand, although none of the bi-benzimidazole extractants described in Examples 2 to 6 of EP 196,153A extracts as much as 40% of the zinc from the aqueous feed solution, the resulting complexes are not of such a strength so that the zinc is readily stripped from the organic phase into the aqueous strip solution. Thus, all the extractants disclosed in EP 196,153A have deficiencies either in terms of extraction or stripping effeciciency.

The extractant of Example 6 of EP 196,153A contains methyl substituents in the benzene ring and extracts no more than 20% of the zinc into the aqueous phase. As this extractant was prepared from a mixture of methyl-1,2-diaminobenzenes having 33% of the methyl groups adjacent to one of the amino groups, a substantial proportion of the methyl substituents will be in the 4- or 7-positions on the benzene rings of the resulting mixture of bibenzimidazoles.

We have found that the present extractants extract more zinc than the bibenzimidazoles of Examples 2-6 or EP 196,153A and, furthermore, that the extracted zinc is more readily stripped from the organic phase than is the case with the bi-imidazole compound of Example 1 of EP 196153. Thus, the present extractants are especially useful for the solvent extraction of zinc from commercially available solutions.

As illustrated by the following Examples, the present extractants provide a range of properties so that a suitable extractant may be selected for use with a given aqueous feed solution. The properties of the present extractants may be modified by mixing them together of by mixing them with one or more other extractants, especially with one of the bi-benzimidazole extractants disclosed in EP 196,153A. Thus, a 5,6,5',6'-tetramethyl-bibenzimidazole compound in accordance with the present invention may be used together with the corresponding bibenzimidazole compound containing no benzene ring substituents, such compounds being disclosed in Examples 1 to 5 of EP 196153. The properties of this mixture may be adjusted by varying the relative proportions of the two extractants.

The extraction process may be effected using a solution of the present extractant in a water-immiscible organic solvent. Examples of suitable water-immiscible organic solvents are aliphatic, aromatic and alicyclic hydrocarbons, chlorinated hydrocarbons such as perchloroethylene, trichloroethane and trichloroethylene. Mixtures of solvents may be used. Especially preferred in conventional hydrometallurgical practice are mixed hydrocarbon solvents such as high boiling, high flash point petroleum fractions (for example kerosena) with varying aromatic content. In general, hydrocarbon solvents having a high aromatic content, for example AROMASOL H which consists essentially of a mixture of trimethylbenzenes and commercially available from Imperial Chemical Industries PLC (AROMASOL is a trade mark) or SOLVESSO 150 commercially available from Esso (SOLVESSO is a trade mark), provide a higher solubility for the extractant and its metal complex, whilst kerosene having a relatively low aromatic content, for example ESCAID 100 which is a petroleum distillate comprising 20% aromatics, 56.6% paraffins and 23.4% naphthenes commercially available from EXXON (ESCAID is a trade mark) may in certain cases improve the hydrometallurgical performance of the extractant. The use of a solvent having a low aromatic content may be preferred on environmental and toxicological grounds. Factors influencing the solubility of the extractant and its metal complex are complicated, but in general extractants having highly branched substituents and/or an isomeric mixture of substituents have comparatively high solubility in hydrocarbon solvents. The concentration of the extractant in the water-immiscible organic solvent may be chosen to suit the particular leach solution to be treated. Typical values for the concentration of the present extractants in the organic phase are from 0.05M to 2M, preferably from 0.1M to 1.0M, and especially from 0.1M to 0.5M, in the organic solvent.

The invention is illustrated by the following Examples in which all parts and percentages are by weight unless otherwise stated.

EXAMPLE 1

The preparation of 1,1'-bis(tridecyloxycarbonyl)-5,6,5',6'-tetramethyl-2,2'-bibenzimidazole.

4,5-Dimethyl-1,2-diaminobenzene (68.7 g) was dissolved in methanol (450 cm³) by warming to 35° C. The solution was stirred while methyl 2,2,2-trichloroacetimidate (44.1 g) was added cautiously. During the addition of the methyl 2,2,2-trichloroacetimidate there is an induction period, following which the reaction can occur violently and hence not more than 10 g of the methyl-2,2,2-trichloroacetimidate was added before a rise in temperature indicated that the induction period was over. The addition of the acetamidate was then continued at such a rate that, with the assistance of external cooling, the reaction temperature was maintained at about 40° C. The mixture was allowed to cool, stirred at 25° C. for 18 hours, and then diluted with water (1 dm³) and filtered. The collected solid was washed with water (700 cm³) and dried over anhydrous calcium chloride at 30° C. to 40° C. and a pressure of 20 mm of mercury to give 64.1 g of a solid product. The solid was purified by continuous extraction with ethanol in a Soxhlet extractor. A crystalline solid precipitated in the extract and was collected and dried over anhydrous calcium chloride as previously described to give a yield of 23.8 g of solid. The solid proved to be the monohydrochloride of 5,6,5',6'-tetramethyl-2,2'-bibenzimidazole by analysis and proton NMR spectroscopy.

Found; C, 65.9; H, 5.5; N, 16.5; Cl, 11.0%; Calculated for $C_{18}H_{19}N_4Cl$: C, 66.2, H, 5.8; N, 17.1; Cl, 10.9%.

The structure was confirmed by measurement of the proton NMR spectrum using a solution in trifluoroacetic acid with tetramethylsilane as an internal standard. This showed peaks at (delta-value, multiplicity, number of protons and assignment given)

| 2.56, | singlet, | 12, | CH₃—Ar; |
| 7.80, | singlet, | 4, | H—Ar. |

The monohydrochloride was converted into the free base in near to theoretical yield by stirring with 2M aqueous $NaCO_3$ (200 cm³) for 18 hours at 70° C., collecting the solid, washing it with water and drying over anhydrous calcium chloride as previously described. 5,6,5',6'-tetramethyl-2,2'-bibenzimidazole (14.5 g, obtained as described) was stirred at 25° C. with dry methylene chloride (200 cm³) and dry pyridine (30 cm³). To this suspension, tridecyl chloroformate (28.9 g, prepared as described in Example 1 of EP 196,153A) was added over 30 minutes, during which time the reaction temperature rose to 32° C. The mixture was stirred for a further 18 hours, diluted with hexane (100 cm³) and extracted with water (100 cm³) in a separating funnel. The hexane solution was successively extracted with aqueous 1M HCl (4×200 cm³ amounts) and then with water (4×200 cm³ amounts), dried with anhydrous magnesium sulphate, treated with active carbon and filtered. The solvents were distilled by thin film evaporation, finally at 90° C. and 0.5 nm Hg mercury pressure, leaving a pale yellow oil (34.0 g). The structure was confirmed to be a mixture of 1,1'-bis(tridecyloxycarbonyl)-5,6,5',6'-tetramethyl-2,2'-bibenzimidazoles by measurement of the proton NMR spectrum using a solution in deuterochloroform with tetramethylsilane as internal standard. This showed peaks at:

(delta-value, multiplicity, number of protons and assignment given)

| 0.5–1.8, | multiplet, | 50, | $C_{12}H_{25}$ groups; |
| 2.33, | singlet, | 6, | CH₃-aryl; |
| 2.38, | singlet, | 6, | CH₃-aryl; |
| 4.1, | multiplet, | 4, | CH₂O—; |
| 7.51, | singlet, | 2, | H-aryl; |
| 7.80, | singlet, | 2, | H-aryl. |

The purity of the composition was estimated by potentiometric titration of a sample with 0.1M perchloric acid in glacial acetic acid solution (when the compound behaved as a monoacid base) and found to be 84% of theoretical for molecular weight 743.1. The purity of the composition was also estimated by contacting a solution containing 0.7604 g of the compound in 10 cm³ of SOLVESSO 150 with an aqueous solution containing about 300 gdm⁻³ of zinc chloride when it was found that 5 cm³ of the organic solution had extracted 0.0271 g of zinc, that is 81% of theoretical for a complex of 1:1 stoichiometry.

EXAMPLE 2

The preparation of a mixture of 1,1'-bis(tridecyloxycarbonyl)-dimethyl-2,2'-bibenzimidazoles in which each benzene ring contains a methyl group in the 5- or 6-position.

3,4-Diaminotoluene (100.8 g) was dissolved in methanol (600 cm³) at room temperature. The solution was stirred while methyl 2,2,2-trichloroacetimidate (70.6 g) was added in a manner similar to that described in Example 1. The mixture was allowed to cool and was stirred at room temperature for 36 hours, then diluted with water (1.5 dm³) and filtered. The solid was added again to water (1 dm³) stirred at room temperature and filtered. The solid was added to aqueous 2N sodium carbonate solution (1 dm³) stirred at 70° C. for 12 hours, cooled and filtered. The solid was repeatedly washed with methanol (3×500 cm³) by slurrying and filtering to leave a pale tan coloured solid. This solid was treated with activated carbon, recrystallised from boiling dimethylformamide, and dried, yielding 49 g of 5,5'-dimethyl-2,2'-bibenzimidazole. By this method the free base rather than the monohydrochloride was isolated (found Cl<0.2%).

The structure was confirmed by measurement of the proton NMR spectrum using a solution in trifluoracetic acid with tetramethylsilane as internal standard. This showed peaks at (delta-value, multiplicity, number of protons, and assignment given)

| 2.68, | singlet, | 6, | CH₃—Ar; |
| 7.60–8.05, | multiplet, | 6, | H—Ar; |
| 12.75, | singlet, | 2, | H—N. |

5,5'-Dimethyl-2,2'-bibenzimidazole (41.42 g, obtained as described) was reacted with tridecylchloroformate (78.85 g) as in Example 1, to give light amber coloured oil (78.5 g). The structure was confirmed to be a mixture of 1,1'-bis(tridecyloxycarbonyl)-5(6),5'(6')-dimethyl-2,2'-bibenzimidazole isomers by measurement of the proton NMR spectrum using a solution in deuterochloroform with tetramethylsilane as internal standard. This showed peaks at: (delta-value, multiplicity, numbers of protons and assignment given)

| 0.5–1.8, | multiplet, | 50, | $C_{12}H_{25}$ groups; |
|---|---|---|---|
| 2.46, | singlet, | 3, | $3CH_3$-aryl; |
| 2.53, | singlet, | 3, | $CH_3$-aryl; |
| 4.2, | br multiplet, | 4, | $CH_2O$—; |
| 7.1–8.0, | multiplet, | 6, | H-aryl; |

The purity of the mixture of isomers was estimated by potentiometric titration as in Example 1 and was found to be 85.7% of theoretical for molecular weight 715.0.

EXAMPLE 3

The preparation of a mixture of 1,1'-bis(isodecyloxycarbonyl)-dimethyl-2,2'-bibenzimidazole in which each benzene ring contains a methyl group in the 5- or 6-position.

3,4-Diaminotoluene (252 g) and concentrated hydrochloric acid (4 cm$^3$) were dissolved in methanol (700 cm$^3$) and heated slowly to reflux while stirring. Trichloroacetonitrile (144.4 g) was added slowly dropwise to maintain a steady reflux rate. After completion of the addition, the mixture was refluxed for 5 hours and then left for 48 hours at room temperature. The mixture was filtered, the solid which was collected was slurried in a mixture of warm (35° C.) water (1.5 cm$^3$) and methanol (200 cm$^3$) for 10 minutes. The stirred slurry was adjusted to pH 9 with concentrated ammonia solution (60 cm$^3$, 0.880 SG) and stirred for a further 15 minutes. The solid was filtered off, washed with warm water (1 cm$^3$) and dried at 60° C. overnight in a vacuum oven under a water vacuum to give 144.5 g of solid. This solid was slurried in methanol (750 cm$^3$) for 2 hours, left to stand without stirring overnight, filtered and dried at 60° C. overnight in a vacuum oven under a water vacuum to give a yellow tan powdery solid (116 g). Analysis by HPLC proved it to be 5,5'-dimethyl-2,2'-bibenzimidazole with a purity of 97% theory for molecular weight of 262.3.

5,5'-Dimethyl-2,2'-bibenzimidazole (52.5 g, obtained as described herein) was reacted with isodecylchloroformate (88.3 g, prepared from commercial mixed isodecanol as described in Example 5 of EP 196153) using the procedure described in Example 1, to give a viscous amber coloured oil (120 g). The structure was confirmed to be a mixture of 1,1'-bis-(isodecyloxycarbonyl)-5(6),5'(6')-dimethyl-2,2'-bibenzimidazoles by measurement of the proton NMR spectrum using a solution in deuterochloroform with tetramethylsilane as internal standard. This showed peaks at: (delta-value, multiplicity, number of protons and assignments given)

| 0.6–1.7, | multiplet, | 38, | $C_9H_{19}$ groups; |
|---|---|---|---|
| 2.50, | singlet & | | |
| 2.55, | singlet, | total 6, | $CH_3$-aryl; |
| 4.2, | multiplet, | 4, | $CH_2O$—; |
| 7.25, | multiplet, | 2, | H-aryl; |
| 7.6, | singlet & | | |
| 7.7, | doublet, | total 2, | H-aryl; |
| 7.9, | multiplet, | 2, | 2H-aryl. |

The purity of the mixture of isomers was estimated by potentiometric titration as in Example 1 and was found to be 96.2% of theoretical for molecular weight 630.9.

EXAMPLE 4

The preparation of a mixture of 1,1'-bis(isooctadecyloxycarbonyl)-dimethyl-2,2'-bibenzimidazoles in which each benzene ring contains a methyl group in the 5- or 6-position.

5,5'-Dimethyl-2,2'-bibenzimidazole (52.5 g, prepared as described in Example 3) was stirred in pyridine (400 cm$^3$) at room temperature for 30 minutes. Isooctadecyl chloroformate 207 g, (prepared as described in Example 2 of EP 196,153A) was added over 45 minutes, during which time the reaction temperature rose to 40° C. The mixture was stirred at room temperature for a further 3 hours, neutralised with concentrated hydrochloric acid (400 cm$^3$) to pH 2.5, diluted with hexane (400 cm$^3$) and stirred for a further 15 minutes. The mixture was filtered and the hexane solution was then extracted with aqueous 1 molar hydrochloric acid (300 cm$^3$) in a separating funnel. The hexane solution was then extracted successively with brine (NaCl solution containing 180 gdm$^{-3}$ NaCl) till acid free (3×350 cm$^3$, to pH 6), dried with anhdrous magnesium sulphate, treated with activated carbon and filtered. The solvent was distilled by thin film evaporation, under reduced pressure (0.2 mm Hg at 95° C. for two hours) leaving a pale yellow very viscous oil (219 g). The structure of this material was confirmed to be a mixture of 1,1'-bis(isooctadecyloxycarbonyl)-5(6),5'(6')-dimethyl-2,2'-bibenzimidazoles by measurement of the proton NMR spectrum using a solution in deuterochloroform with tetramethylsilane as internal standard. This showed peaks at: (delta-value, multiplicity, number of protons and assignment given)

| 0.6–1.7, | multiplet, | 70, | $C_7H_{35}$ groups; |
|---|---|---|---|
| 2.43, | singlet & | | |
| 2.46, | singlet, | total 6, | $CH_3$-aryl; |
| 4.1, | multiplet, | 4, | $OCH_2$—; |
| 7.16, | multiplet, | 2, | H-aryl; |
| 7.54, | singlet & | | |
| 7.62, | doublet, | total 2, | H-aryl; |
| 7.85, | multiplet, | 2, | H-aryl. |

The purity of the compound was estimated by potentiometric titration, as described in Example 1 and found to be 83% of theoretical for molecular weight 851.3.

COMPARATIVE EXAMPLE A

The preparation of a mixture of 1,1'-bis(tridecyloxycarbonyl)-dimethyl-2,2'-bibenzimidazoles in which each benzene ring contains a methyl group in the 4- or 7-position.

2,3-Diaminotoluene (20 g, 0.16 moles) and concentrated hydrochloric acid (0.5 cm$^3$) were stirred in methanol (100 cm$^3$) and trichloroacetonitrile (8 cm$^3$) was added dropwise over the course of 20 minutes. The mixture was heated under reflux for 18 hours. On cooling the reaction mixture was brought to pH 9 by the addition of dilute ammonia solution, the slurry was stirred for 15 minutes and then the solid was collected by filtration. The solid was twice slurried with 100 cm$^3$ of water, filtered and dried at 60° C. overnight in a vacuum oven under a water vacuum.

4,4'-Dimethylbibenzimidazole (5.53 g) was stirred in pyridine (40 cm$^3$) and reacted with tridecylchloroformte (5.54 g) and the product recovered as generally described in Example 4 to yield a greenish yellow oil. The oil was identified by its proton NMR spectrum as a mixture of 1,1'-bis(tridecyloxycarbonyl)-4,(7),4'(7')-dimethylbibenzimidazole isomers using a solution in deuterochloroform with tetramethylsilane as internal standard. This showed peaks at: (delta-value, multiplicity, number of protons and assignments given)

| | | | |
|---|---|---|---|
| 0.6–1.8, | multiplet, | 50, | C$_{12}$H$_{25}$ groups; |
| 2.6, | singlet, | 6, | CH$_3$-aryl; |
| 4.1, | multiplet, | 4, | O—CH$_2$—; |
| 7.15, | doublet, | 2, | H-aryl; |
| 7.26, | 2 × doublet, | 2, | H-aryl (6-position); |
| 7.85, | doublet, | 2, | H-aryl. |

EXAMPLES 5 to 8 and COMPARATIVE EXAMPLE B

The ability of the compositions of Examples 1 to 4 (hereinafter referred to as Extractants 1 to 4) and in Comparative Example A (Extractant A) to extract zinc from aqueous solutions containing chloride ion was investigated by the following general method.

An aqueous solution was prepared which was 0.6M in zinc chloride (39 gdm$^{-3}$ zinc), 0.1M in HCl and which contained 626.5 gdm$^{-3}$ CaCl$_2$ dihydrate. A portion of this solution was stirred vigorously for 1.5 minutes at ambient temperature with an equal volume of a solution which was a 0.2M solution of the extractant in the aromatic hydrocarbon solvent SOLVESSO 150. The layers were allowed to separate and were separately analysed for zinc content. The transfer of zinc from the aqueous to the organic phase was calculated as a percentage of the amount that could theoretically be taken up by the extractant (L), assuming the formation of a complex LZnCl$_2$. The results obtained are set out in Table One, together with results obtained using the Extractant A.

TABLE ONE

| Example or Comp Example | Extractant | % Theoretical zinc update |
|---|---|---|
| 5 | 1 | 87.6% |
| 6 | 2 | 56.1% |
| 7 | 3 | 63.3% |
| 8 | 4 | 36.2% |
| B | A | 0.0 |

It will be observed that Extractant 1 (tetramethyl derivative) is a more powerful extractant for zinc than the Extractant 2 [5,(6), 5'(6')-dimethyl derivative]. It will also be observed that the nature of the alkyloxycarbonyl group affects the amount of zinc extracted under the test conditions. The use of the 4(7),4'(7')-dimethyl derivative, Extractant A, results in no extraction of zinc, indicating the effect of the position of the methyl substituent in the benzene ring.

EXAMPLES 9 to 11

These examples demonstrate the selectivity of Etractants 2 to 4 for zinc over iron and other metals.

An aqueous feed solution was prepared simulating one that might be obtained by i) leaching a zinc bearing complex ore with ferric chloride solution and ii) removing most of the copper originally present in the leach liquor by solvent extraction and cementation. Portions of this aqueous feed solution were contacted by vigorous stirring for one hour at 25° C. with equal volumes of 0.25M solutions of the extractants in the high flash point hydrocarbon diluent Escaid 100. The phases were allowed to settle and portions of each organic phase sampled and analysed quantitatively for the metals known to be present in the aqueous feed. The results are as shown in Table Two.

TABLE TWO

| Example | Solution (a) | Metals (mgdm$^{-3}$) | | | | |
|---|---|---|---|---|---|---|
| | | Zn | Fe (II) | Pb | Sb | Cu |
| — | Aq | 50,000 | 110,000 | 1,500 | 25 | 25 |
| 9 | Org 2 | 12,500 | 12 | <1 | <10 | 18 |
| 10 | Org 3 | 12,500 | 5 | <1 | <10 | 19 |
| 11 | Org 4 | 11,000 | 1 | <1 | <10 | 11 |

Notes To Table Two
Aq is the aqueous feed solution
Org 2 is 0.25M solution of Extractant 2 in Escaid 100.
Org 3 is 0.25M solution of Extractant 3 in Escaid 100.
Org 4 is 0.25M solution of Extractant 4 in Escaid 100.

EXAMPLE 12

This example illustrates the utility of Extractant 2 in a solvent extraction process for recovery of zinc based on extraction from a zinc bearing feed solution and stripping the zinc back into an aqueous stream of a type from which zinc may be subsequently recovered, for example by electrowinning.

Portions of an aqueous zinc bearing solution containing 50 gdm$^{-3}$ zinc, 5 gdm$^{-3}$ HCl, and a total chloride ion concentration of 5.5M were contacted at a range of organic to aqueous phase ratios with 0.25M solution in Escaid 100 of Extractant 2. Stirring was maintained for one hour at a temperature of 25° C. after which the phases were allowed to settle and then separated. Each organic and aqueous phase was analysed for zinc. The results are as shown in Table Three.

TABLE THREE

| Organic to aqueous volume ratios | 12:1 | 6:1 | 3:1 | 2:1 | 1:1 | 1:3 | 1:6 | 1:8 |
|---|---|---|---|---|---|---|---|---|
| Zinc in organic (gdm$^{-3}$) | 3.06 | 5.43 | 8.30 | 9.95 | 11.56 | 12.59 | 12.96 | 13.02 |
| Zinc in aqueous (gdm$^{-3}$) | 11.96 | 17.42 | 24.38 | 29.81 | 38.96 | 45.60 | 47.80 | 49.09 |

The facility of stripping zinc from the zinc loaded extractant phase to produce a concentrated zinc electrolyte solution was demonstrated as follows. A 0.25M solution, in Escaid 100, of Extractant 2, was loaded with zinc to a level of 13.0 gdm$^{-3}$ by two successive contacts, each with an equal volume of an aqueous solution containing 50 gdm$^{-3}$ zinc, and 5.5M in chloride ion. Portions of the zinc loaded organic solution were contacted at various volume ratios with an aqueous strip solution containing 30 gdm$^{-3}$ of zinc, as zinc chloride, and 5 gdm$^{-3}$ hydrochloric acid. Contacting was carried out by stirring vigorously at 60° C. for one hour, after which the phases were allowed to settle and separate. Both phases were analysed for zinc. The results are shown in Table Four.

TABLE FOUR

| Organic to aqueous phase ratio | 6:1 | 2:1 | 1:1 | 1:2 |
|---|---|---|---|---|
| Zinc in organic (gdm$^{-3}$) | 5.88 | 2.81 | 1.70 | 1.14 |
| Zinc in aqueous (gdm$^{-3}$) | 74.7 | 51.7 | 41.8 | 36.4 |

EXAMPLE 13

The procedure of Example 12 was repeated with the exception that the aqueous strip solution contained 30 gdm$^{-3}$ zinc, as zinc chloride, 5 gdm$^{-3}$ HCl and 110 gdm$^{-3}$ sodium chloride. This strip solution represents a possible spent electrolyte from an electrowinning process. The results are shown in Table Five.

TABLE FIVE

| Organic to aqueous phase ratio | 6:1 | 2:1 | 1:1 | 1:2 |
|---|---|---|---|---|
| Zinc in organic (gdm$^{-3}$) | 7.15 | 4.31 | 3.03 | 2.48 |
| Zinc in aqueous (gdm$^{-3}$) | 65.7 | 48.3 | 39.9 | 35.6 |

We claim:

1. A composition of bibenzimidazoles of the Formula (I):

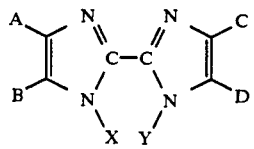

wherein

X & Y which may be the same or different and, taken together, contain a total of from 12 to 52 saturated carbon atoms, are (a) each selected from —R, —COR, —CH$_2$COOR, —CH(COOR)$_2$ and —COOR; or (b) together form a group selected from

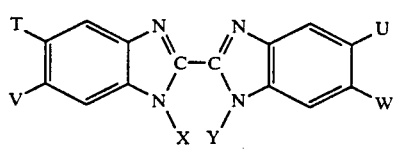

wherein is a hydrocarbyl group which is unsubstituted or substituted by C$_1$-C$_8$ alkoxy or halogen, A & B taken together with the two carbon atoms to which they are linked form a benzene ring which is unsubstituted or substituted by C$_1$-C$_6$ alkyl or C$_1$-C$_6$ alkoxy;

characterised in that at least 50% by weight of the bibenzimidazoles in the composition are of Formula (II) wherein X and Y are as hereinbefore defined;

T, U, V & W which may be the same or different, are H, R$^1$ or$^1$ provided at least one of T, U, V & W is R$^1$ or$^1$;

and R$^1$ is C$_1$-C$_6$-alkyl.

2. A composition comprising a compound of Formula (IIa) and a compound of Formula (IIb) in a weight ratio of at least 3 to 1; respectively

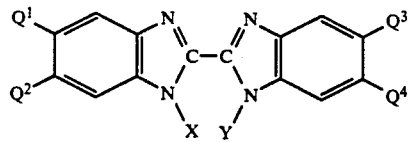

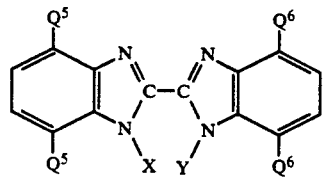

wherein

Q$^1$, Q$^2$, Q$^3$ and Q$^4$ are each independently H, alkyl or alkoxy;

X and Y are as defined in claim 1; and one of the groups represented by Q$^5$ and one of the groups represented by Q$^6$ are each methyl and all remaining groups represented by Q$^5$ and Q$^6$ are H; provided that at least one of Q$^1$, Q$^2$, Q$^3$ and Q$^4$ is alkyl or alkoxy.

3. A composition according to claim 2 which is free or substantially free from any compound of formula (IIb).

4. A compound of Formula (II)

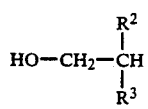

wherein

X and Y are as defined in claim 1;

T, U, V & W which may be the same or different are C$_{1-6}$-alkyl or C$_{1-6}$-alkoxy.

5. A composition according to claim 1 wherein X and Y are both —COOR.

6. A composition according to claim 1 wherein R is alkyl containing up to 24 carbon atoms.

7. A composition as claimed in claim 6 wherein R is branched C$_{8-24}$-alkyl.

8. A composition according to claim 7 wherein R is a branched primary alkyl group.

9. A composition according to claim 7 wherein the groups represented by R in the same molecule or in different molecules in the composition are isomeric alkyl groups.

10. A composition according to claim 8 wherein R is derived from primary alcohols having the general formula (III)

$$HO-CH_2-\underset{R^3}{\underset{|}{\overset{R^2}{\overset{|}{CH}}}}$$

(III)

wherein

R$^2$ and R$^3$ are both alkyl groups and one of the groups R$^2$ and R$^3$ contains two fewer carbon atoms than the other one of groups R$^2$ and R$^3$.

11. A compound according to claim 1 wherein R$^1$ is C$_{1-4}$-alkyl.

12. A compound according to claim 1 carrying at least one group $R^1$ or $OR^1$ on each benzene ring.

13. A composition according to claim 1 wherein the compound of Formula (II) is selected from 1,1'-bis(tridecyloxycarbonyl)-5,5',6,6'-tetramethyl-2,2'-bibenzimidazole;

1,1'-bis(tridecyloxycarbonyl)-5(6),5'(6')-dimethyl-2,2'-bibenzimidazole;

1,1'-bis(isodecyloxycarbonyl)-5(6),5'(6')-dimethyl-2,2'-bibenzimidazole;

1,1'-bis(isooctadecyloxycarbonyl)-5(6),5'(6')-dimethyl-2,2'-bibenzimidazole.

14. The compound 1,1'-bis(tridecyloxycarbonyl)-5,5',6,6'-tetramethyl-2,2'-bibenzimidazole.

* * * * *